United States Patent
Pettis

(10) Patent No.: US 9,186,225 B1
(45) Date of Patent: Nov. 17, 2015

(54) SKIN MARKING DEVICE FOR RADIOGRAPHIC IMAGING

(71) Applicant: Christopher Pettis, Orlando, FL (US)

(72) Inventor: Christopher Pettis, Orlando, FL (US)

( * ) Notice: Subject to any disclaimer, the term of this patent is extended or adjusted under 35 U.S.C. 154(b) by 47 days.

(21) Appl. No.: 14/299,806

(22) Filed: Jun. 9, 2014

(51) Int. Cl.
*A61B 19/00* (2006.01)

(52) U.S. Cl.
CPC .......... *A61B 19/54* (2013.01); *A61B 2019/545* (2013.01); *A61B 2019/5466* (2013.01)

(58) Field of Classification Search
CPC .......... A61B 17/1764; A61B 17/3403; A61B 2017/3411; A61B 2019/5238; A61B 2019/5466; A61B 19/54
See application file for complete search history.

(56) References Cited

U.S. PATENT DOCUMENTS

| | | |
|---|---|---|
| 4,841,967 A | 6/1989 | Chang et al. |
| 4,860,331 A | 8/1989 | Williams et al. |
| 4,985,019 A | 1/1991 | Michelson |
| 5,047,036 A | 9/1991 | Koutrouvelis |
| 5,196,019 A | 3/1993 | Davis et al. |
| 5,306,271 A | 4/1994 | Zinreich et al. |
| 5,469,847 A | 11/1995 | Zinreich et al. |
| 5,961,455 A | 10/1999 | Daum et al. |
| 6,269,148 B1 | 7/2001 | Jessop et al. |
| 7,169,155 B2 | 1/2007 | Chu et al. |
| 7,751,868 B2 | 7/2010 | Glossop |
| 2005/0234322 A1 | 10/2005 | Lober |
| 2009/0253981 A1 | 10/2009 | Hamilton et al. |
| 2010/0099980 A1 | 4/2010 | Godara et al. |
| 2011/0190787 A1 | 8/2011 | Sahni |
| 2012/0022368 A1 | 1/2012 | Brabrand et al. |
| 2012/0259204 A1 | 10/2012 | Carrat et al. |
| 2012/0302863 A1 | 11/2012 | O'Neill |

FOREIGN PATENT DOCUMENTS

| | | |
|---|---|---|
| WO | 2012088535 A1 | 6/2012 |
| WO | 2014032171 A1 | 3/2014 |

OTHER PUBLICATIONS http://www.mdconsult.com; accessed Apr. 3, 2014.

*Primary Examiner* — Mark Remaly
(74) *Attorney, Agent, or Firm* — Courtney M. Dunn; Lowndes, Drosdick, Doster, Kantor & Reed, P.A.

(57) ABSTRACT

A skin marking device that can be used in radiographic imaging comprising a platform having a handle, a marking member that extends from the handle over the platform, and radiographic markings. The platform has an opening that one end of the marking member is positioned over. The marking member also has a marking pad deployed on that end. When the marking member is depressed, at least a portion of the marking member extends into the opening in the platform allowing the marking pad to protrude from the opposite side of the platform. In use, the device is placed on or near a patient's skin during radiographic imaging and the radiopaque markings are used to assist in proper placement of the device. Once proper placement is achieved, the marking member is depressed, which presses the marking pad through the opening to mark the patient's skin at the desired location.

28 Claims, 7 Drawing Sheets

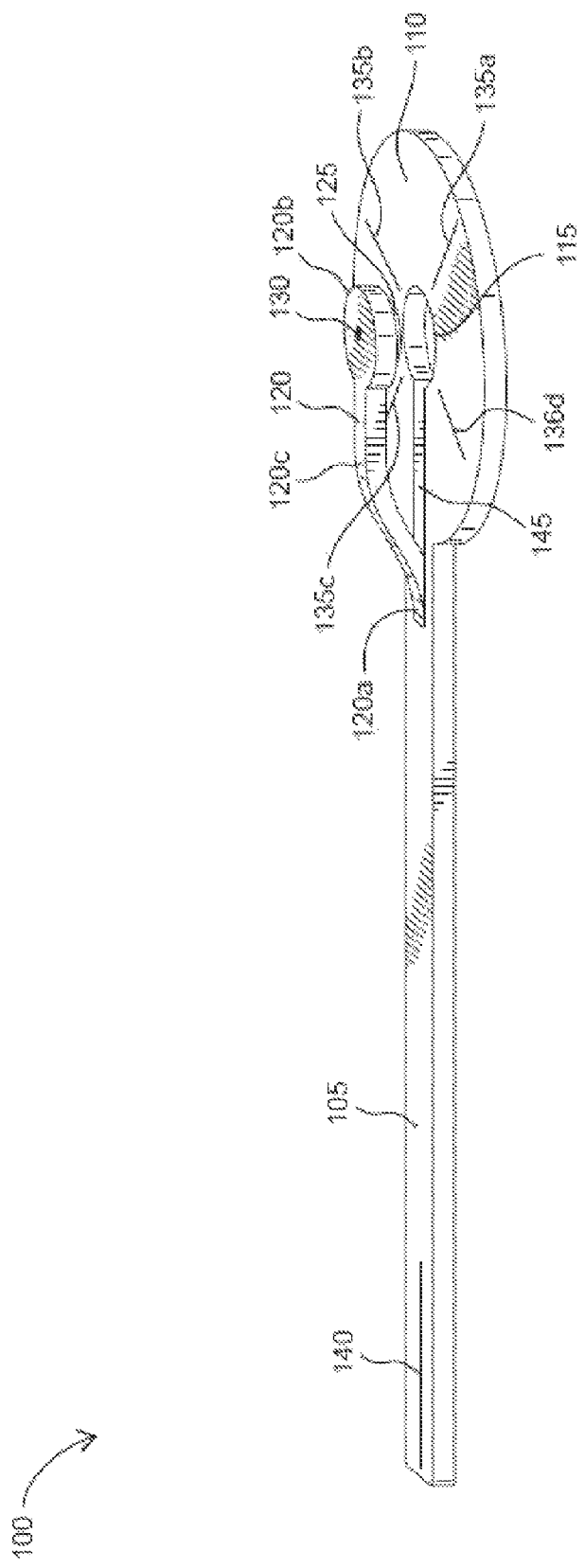

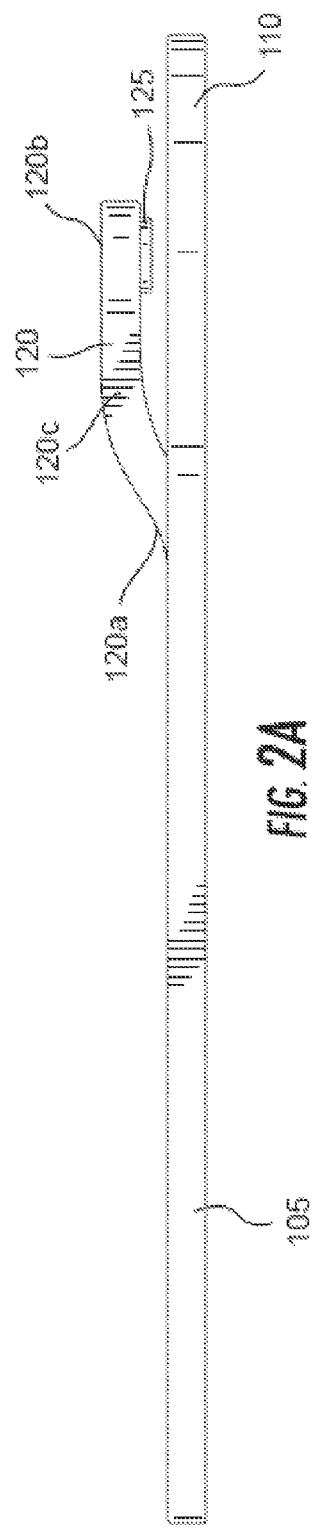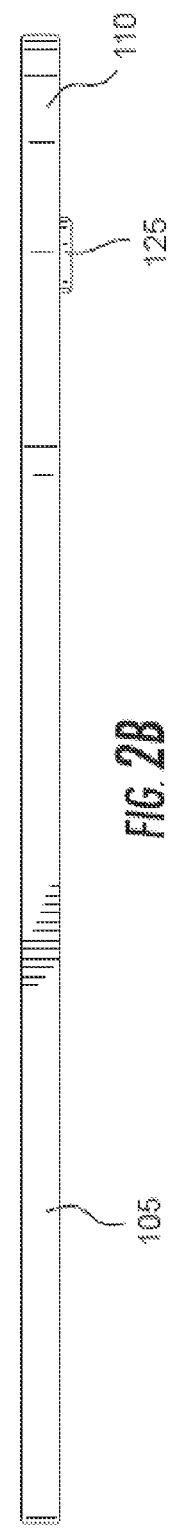

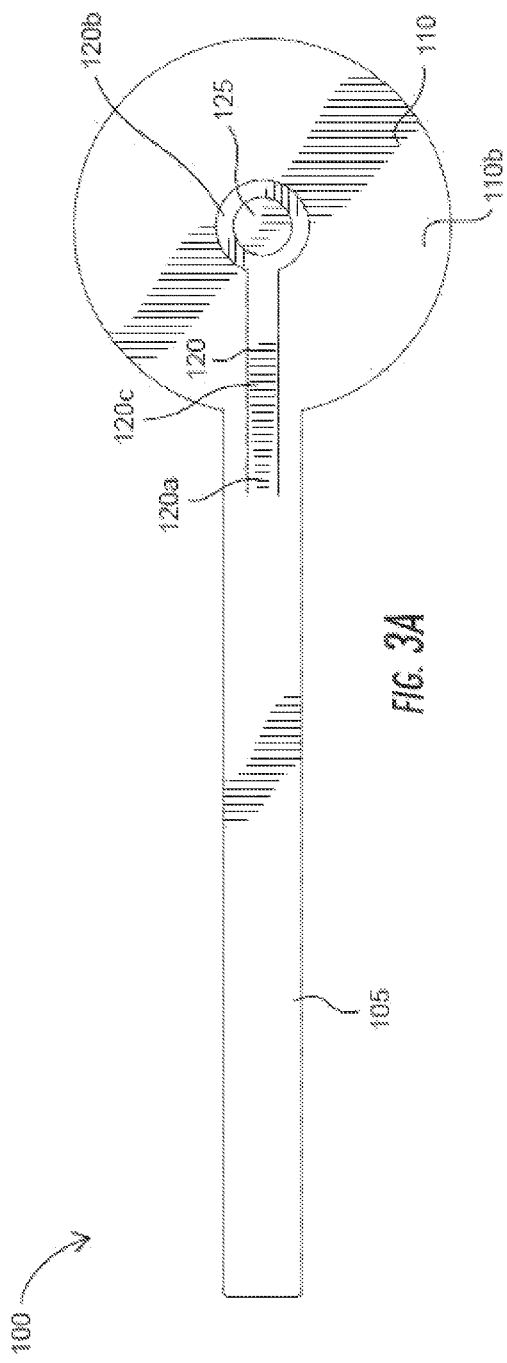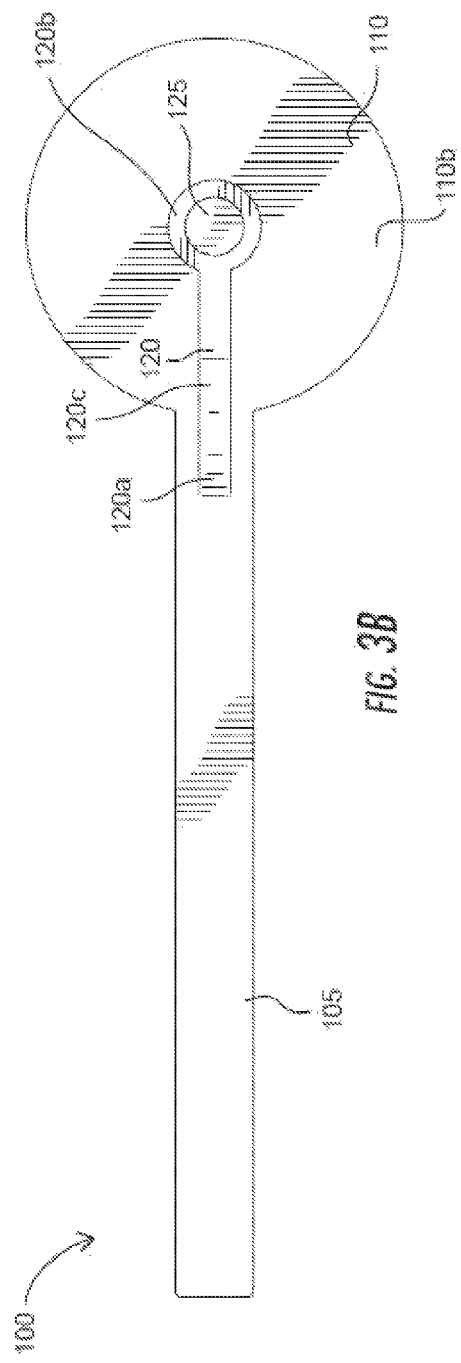

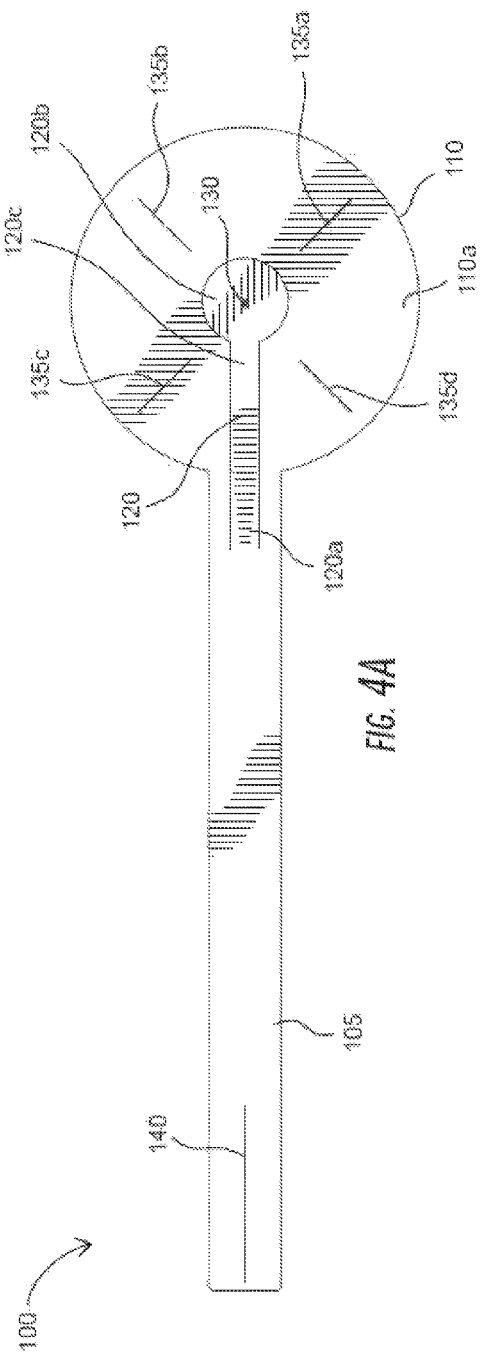
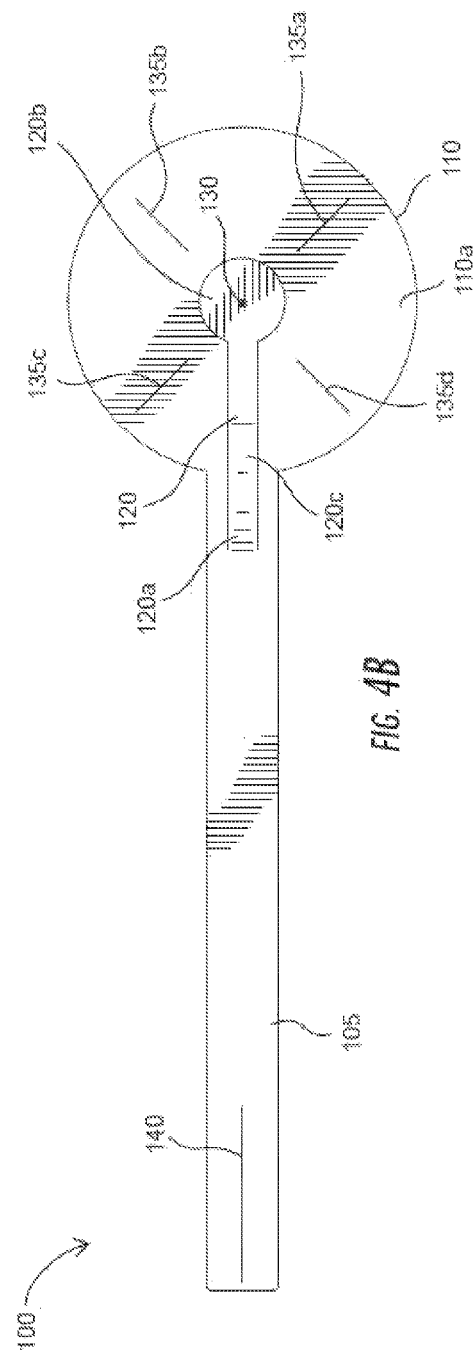

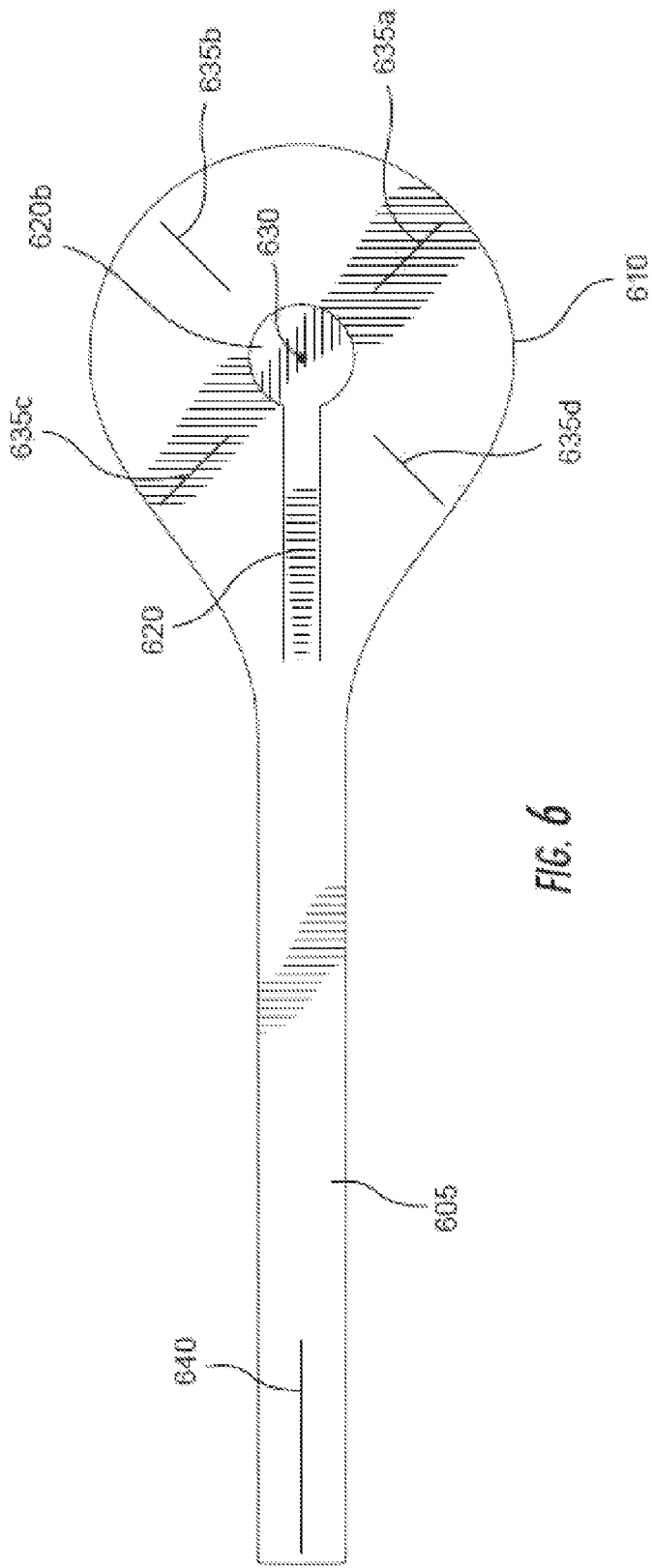

SKIN MARKING DEVICE FOR RADIOGRAPHIC IMAGING

FIELD OF INVENTION

The present disclosure generally relates to devices used to determine proper needle placement in the field of radiology; more specifically, to a skin marking device for use during radiographic imaging.

BACKGROUND

A number of radiographic imaging methods are currently used to visualize radiopaque structures in the human body. These imaging methods are used to help diagnose disease and to guide therapeutic procedures. Exemplary radiographic imaging methods include radiographs, fluoroscopy, and computed tomography (CT).

When using these imaging methods to create images of internal structures, anatomical features that are visible on the patient and on the image can be used as points of reference for determining proper location for needle insertion through the skin or for other surgical or therapeutic procedures. In these cases, a metallic or other radiopaque instrument, such as, for example, a hemostat, paperclip or needle, and a skin marking device, usually in the form of a skin marking pen, are used to locate and mark a specific location on the skin surface. Since the radiopaque instrument will be visible in the image, the instrument is placed over a patient's body and repositioned during imaging until the radiopaque instrument overlies the desired radiopaque point of reference in the human body, usually a bony structure when using fluoroscopy, and then the marking device is used to mark the location on the patient's skin. This marking procedure typically requires two hands and exposes the individual performing the procedure, such as, for example, a physician or technician, to increased radiation because one or both of their hands are near the imaging field for a prolonged period. Once the procedure is completed, the radiopaque instrument and the marking device are typically disposed of. Occasionally, the radiopaque instrument is resterilized at a significant cost and reused. Simply reusing the same radiopaque instrument and pen on multiple patients introduces the risk of infection being spread between patients and many hospitals have instituted policies prohibiting this.

SUMMARY

In accordance with the teachings disclosed herein, embodiments related to a skin marking device for radiographic imaging are disclosed.

In an embodiment, the skin marking device comprises a handle, a platform positioned in communication with the handle, and a marking member extending from the device. The marking member has a first end and a second end and is connected to the device at the first end. A marking pad is positioned on the second end of the marking member. The marking member has a raised state and a depressed state. When the marking member is in its raised state, the second end of the marking member is substantially parallel to and spaced apart from the device. The platform includes an opening that is sized to receive at least a portion of the second end of the marking member. When the marking member is in its depressed state, at least of portion of the second end of the marking member extends into the opening in the platform.

In another embodiment, the skin marking device comprises a handle, a platform positioned in communication with the handle, and a marking member extending from the handle. The marking member has a first end and a second end and is connected to the handle at the first end. A marking pad is positioned on the second end of the marking member. The marking member has a raised state and a depressed state. When the marking member is in its raised state, the second end of the marking member is substantially parallel to and spaced apart from the platform. The platform includes an opening that is sized to receive at least a portion of the second end of the marking member. When the marking member is in its depressed state, at least of portion of the second end of the marking member extends into the opening in the platform.

In an additional embodiment, the skin marking device comprises a platform, a marking member extending from the platform. The marking member has a first end and a second end and is connected to the platform at the first end. A marking pad is positioned on the second end of the marking member. The marking member has a raised state and a depressed state. When the marking member is in its raised state, the second end of the marking member is substantially parallel to and spaced apart from the platform. The platform includes an opening that is sized to receive at least a portion of the second end of the marking member. When the marking member is in its depressed state, at least of portion of the second end of the marking member extends into the opening in the platform.

In a further embodiment, the skin marking device comprises a handle, a disk-shaped platform positioned at an end of the handle, and a marking member extending from the handle. The marking member has a first end and a second end and is connected to the handle at the first end. A marking pad is positioned on a bottom side of the second end of the marking member. The second end of the marking member is circular in shape. The marking member has a raised state and a depressed state. When the marking member is in its raised state, the second end of the marking member is substantially parallel to and spaced apart from the disk-shaped platform. The platform includes a circular opening centered in the disk-shaped platform that has a diameter not smaller than the diameter of the second end of the marking member. The platform also includes a channel extending from the circular opening to the first end of the marking member. When the marking member is in its depressed state, at least of portion of the marking member extends into the channel and the circular opening.

BRIEF DESCRIPTION OF THE DRAWINGS

FIG. 1 is a perspective view of a skin marking device for radiographic imaging according to an embodiment of the present invention.

FIG. 2A is a side elevational view of a skin marking device for radiographic imaging with the marking member in its raised (or non-depressed) state according to an embodiment of the present invention.

FIG. 2B is a side elevational view of a skin marking device for radiographic imaging with the marking member in its depressed state according to an embodiment of the present invention.

FIG. 3A is a bottom plan view of a skin marking device for radiographic imaging with the marking member in its raised state according to an embodiment of the present invention.

FIG. 3B is a bottom plan view of a skin marking device for radiographic imaging with the marking member in its depressed state according to an embodiment of the present invention.

FIG. 4A is a top plan view of a skin marking device for radiographic imaging with the marking member in its raised state and also illustrating an arrangement of radiopaque markings on the handle, marking member, and platform according to an embodiment of the present invention.

FIG. 4B is a top plan view of a skin marking device for radiographic imaging with the marking member in its depressed state and also illustrating the same arrangement of radiopaque markings as shown in FIG. 4A according to an embodiment of the present invention.

FIG. 6 is a top plan view of a skin marking device for radiographic imaging illustrating an alternative handle-to-platform transition according to an embodiment of the present invention.

DETAILED DESCRIPTION OF THE PREFERRED EMBODIMENTS

Figure 5A:
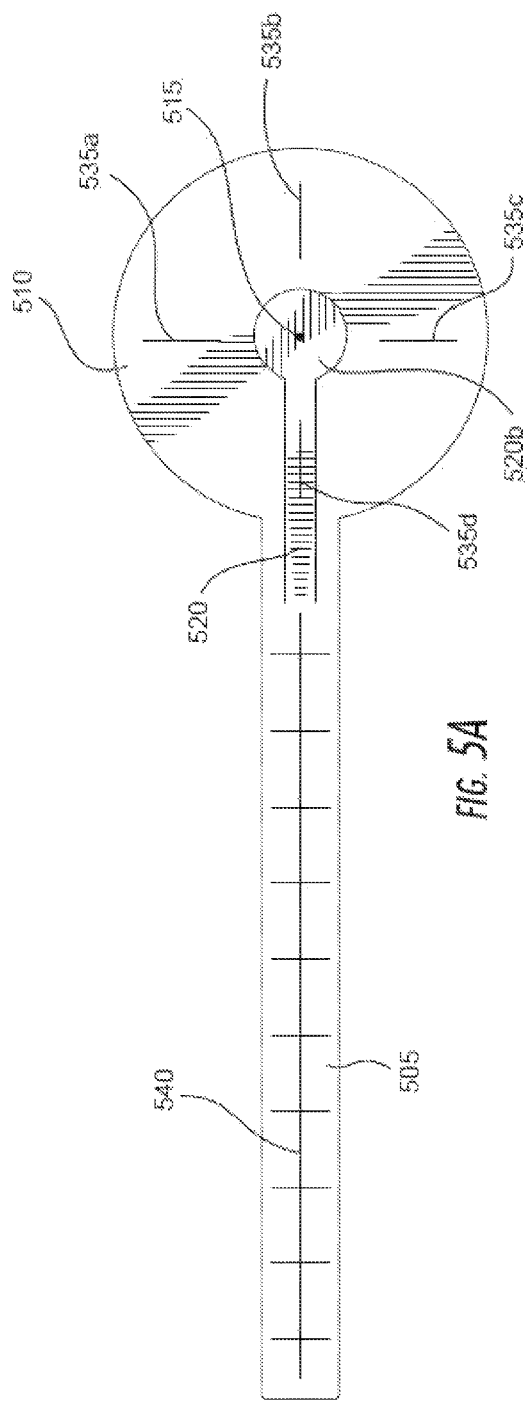
FIG. 5A is a top plan view of a skin marking device for radiographic imaging illustrating another arrangement of radiopaque markings on the handle, marking member, and platform according to an embodiment of the present invention.

A detailed description of the embodiments for a skin marking device for radiographic imaging will now be presented with reference to FIGS. 1 through 7. One of skill in the art will recognize that these embodiments are not intended to be limitations on the scope, and that modifications are possible without departing from the spirit thereof. In certain instances, well-known methods, procedures, components, and circuits have not been described in detail.

Embodiments of the present invention can be used to mark a patient's skin during radiographic imaging.

In an embodiment, as shown with reference to FIGS. 1 through 4B, device 100 includes handle 105, platform 110 located at one end of handle 105, and marking member 120 extending from handle 105. Marking member 120 has first end 120a, second end 120b, and middle portion 120c. First end 120a connects marking member 120 to handle 105. Marking pad 125 is deployed on the bottom side of second end 120b. Platform 110 has opening 115 and channel 145 extending from opening 115 to first end 120a of marking member 120. Opening 115 is sized to receive at least a portion of second end 120b of marking member 120. Channel 145 is sized to receive at least a portion of middle portion 120c of marking member 120. Marking member 120 is bendable and can be moved from a raised, or non-depressed state, which is its relaxed state, to a depressed state.

When marking member 120 is in its raised or non-depressed state, as shown in FIGS. 1, 2A (side view), 3A (bottom view), and 4A (top view), second end 120b is substantially parallel to and spaced apart from platform 110. In the raised state, second end 120b, hovers, at least in part, over opening 115.

When marking member 120 is in its depressed state, as shown in FIGS. 2B (side view), 3B (bottom view), and 4B (top view), at least a portion of second end 120b extends into opening 115. Middle portion 120c of marking member 120 may extend partially or wholly into channel 145 when marking member is in its depressed state.

Marking member 120 can be a seamless and continuous extension of handle 105 (or platform 110 if no handle is present) or it can be a separate piece that is fastened to handle 105 (or platform 110) by known means. Similarly, platform 110 can be a seamless and continuous extension of handle 105 or it can be a separate piece that is fastened to handle 105 by known means.

Marking pad 125 can contain any material that can mark the patient's skin. Exemplary materials include any kind of skin safe ink, such as, for example Gentian violet. Alternatively, marking pad 125 can include a protrusion that indents the skin and causes a temporary depression on the skin that is visible for a period of time. When marking member 120 is depressed, marking pad 125 protrudes at least partially from bottom side 110b (FIGS. 3A and 3B) of platform 110. In use, device 100 will be placed on or near patient's skin with bottom side 110b facing the patient. Radiographic imaging methods are then used to provide images of the patient. Marking device 100 can be moved during imaging and radiopaque markings 130, 140 and 135a-d will guide an individual during imaging. Once the individual locates the designated location using radiopaque markings 130, 140 and 135a-d, the individual can depress marking member which will press marking pad 125 against patient's skin, thereby marking the patient's skin at the desired location.

Second end 120b, as shown in the drawings, may comprise a circular shape; however, this should not be construed as limiting—second end 120b could take on a variety of shape and sizes. Opening 115 can be circular in shape, as shown in the drawings; however, this should not be construed as limiting—opening 115 can take on a variety of shapes and sizes. Opening 115 is open from top side 110a of platform 110 to bottom side 110b of platform 110. Opening 115 and second end 120b should be of appropriate shape and size such that, when marking member 120 is depressed, second end 120b can extend, at least partially, into opening 115 and allow marking pad 125 to protrude, at least partially, from bottom side 110b of platform 110 as best illustrated in FIG. 2B. In the exemplary embodiments shown in the drawings, this is done by providing a marking device with a circular second end and a circular opening in the platform that has a diameter that is larger than or equal to (i.e., not smaller than) the diameter of the circular second end.

Channel 145 may be enclosed on bottom side 110b or it may be completely open from top side 110a to bottom side 110b. Channel 145 is sized to receive, at least in part, middle portion 120c of marking member 120. Channel 145 is optional. In embodiments not including a channel, the second end of the marking member would still at least partially enter the opening when marking member was in its depressed position.

Handle 105 can, as shown, extend length wise out from platform 110, to make a sufficient gripping area for a user. The handle can be made shorter or longer depending on the needs of the user. Alternatively, device 100 can be formed from platform 110 without the inclusion of handle 105. In this embodiment, marking member 120 would extend from platform 110 instead of handle 105.

Figure 7:
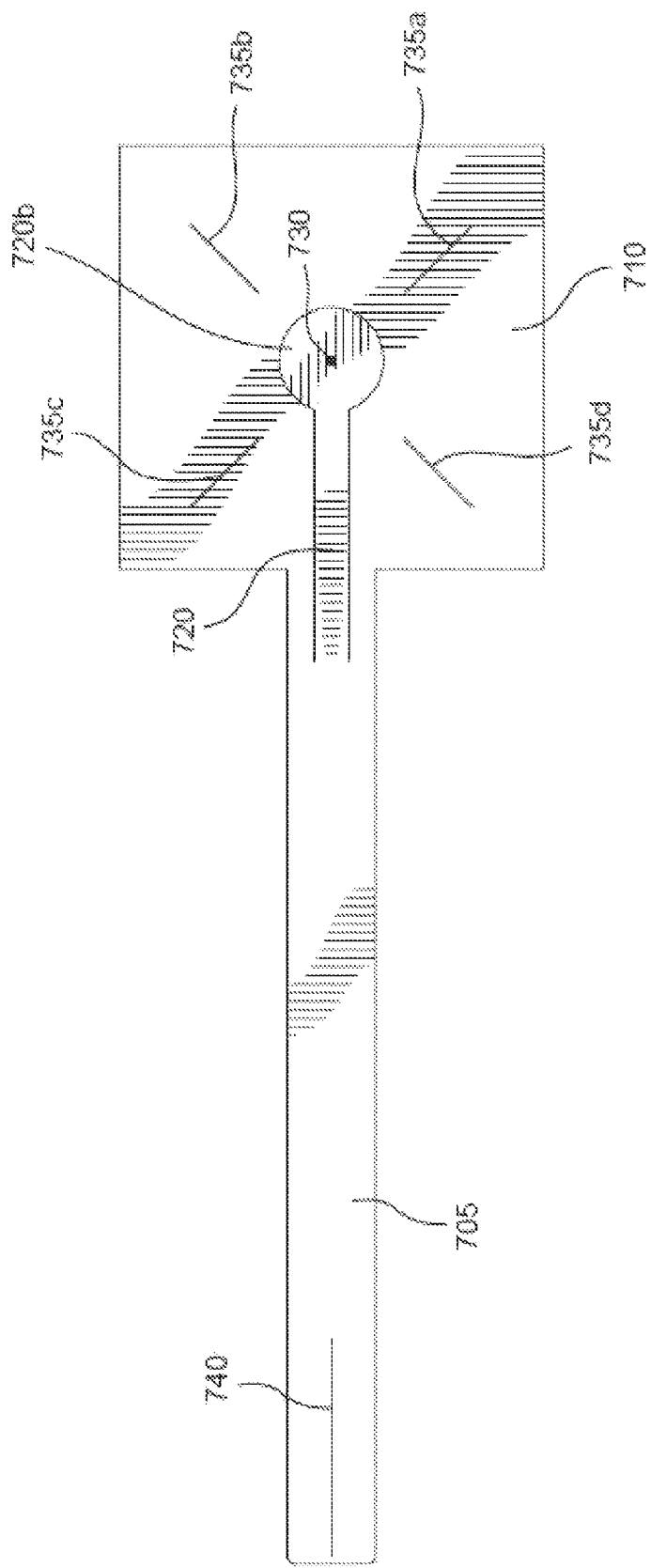
FIG. 7 is a top plan view of a skin marking device for radiographic imaging illustrating an alternative platform shape according to an embodiment of the present invention.

Platform 110, as shown in FIGS. 1 through 5, can be circular, or disk-shaped; however, this should not be construed as limiting. Platform 110 could take on a variety of shapes and sizes. For example, FIG. 7 shows an alternative square shape for platform 710. An alternative handle-to-platform transition can also be used, as illustrated in FIG. 7, which utilizes a partially-circular shape for platform 610.

Radiopaque markings are included in embodiments. As used herein, "radiopaque" includes any substance that at least partially prevents transmission (by blocking, reflecting, absorbing, defracting, and/or any similar phenomena) of at least one type of electromagnetic radiation, such that an image of the substance will be visible in radiographic images. Radiopaque markings using radiopaque materials can be used to assist a user in proper placement of the skin marking device during radiographic imaging. The radiopaque markings used can be of any shape or size and can be made from any known radiopaque material. Exemplary radiopaque materials include titanium, platinum, tungsten, barium sulfate, zirconium oxide, bismuth subcarbonate, stainless steel and iodine.

Figure 5B:
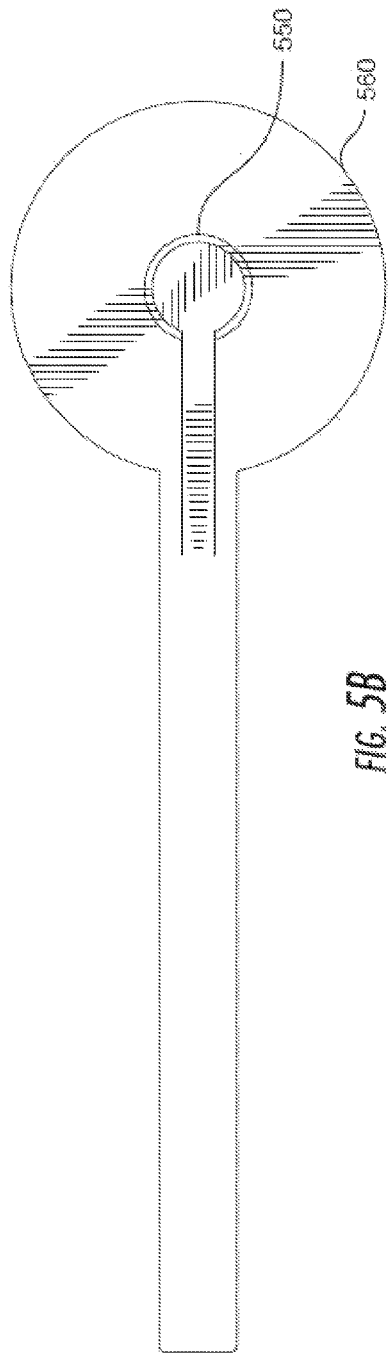
FIG. 5B is a top plan view of a skin marking device for radiographic imaging illustrating yet another arrangement of radiopaque markings on the platform according to an embodiment of the present invention.

Exemplary placement of radiopaque marking are shown in the drawings. In FIGS. 1, 4A and 4B, radiopaque marking 140 is a line on handle 105, radiopaque markings 135a-d are lines in a crosshair formation on platform 110 around opening 115, and radiopaque marking 130 is a dot on second end 120b of marking member 120. In FIG. 5A, radiopaque marking 540 is a grid pattern on the top side of handle 505, radiopaque markings 535a-d are lines in a crosshair formation on platform 510 (radiopaque markings 535a-c) and marking member 520 (radiopaque marking 535d), and radiopaque marking 515 is a dot on second end 520b of marking member 520. In FIG. 5B, radiopaque marking 550 is a ring around the opening (not shown) in platform 560. In FIG. 6, radiopaque marking 640 is a line on handle 605, radiopaque markings 635a-d are lines in a crosshair formation on platform 610 around the opening (not shown), and radiopaque marking 630 is a dot on second end 620b of marking member 620. Similarly, in FIG. 7, radiopaque marking 740 is a line on handle 705, radiopaque markings 735a-d are lines in a crosshair formation on platform 710 around the opening (not shown), and radiopaque marking 730 is a dot on second end 720b of marking member 720.

Embodiments of the present invention can be operated using one hand, can be constructed of lightweight materials, and/or have radiopaque markings and a marking pad that are in fixed relation with one another. This allows one or more positions to be marked quickly and accurately, which can reduce the amount of exposure to both the individual performing the marking and the patient.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A skin marking device comprising:
   a handle;
   a platform positioned in communication with the handle;
   a marking member, having a first end and a second end, extending from the device, wherein the marking member has a raised state and a depressed state, the first end of the marking member is connected to the device, and the second end of the marking member is substantially parallel to and raised above the device when the marking member is in its raised state;
   an opening positioned in the platform, wherein the opening is sized to receive at least a portion of the second end of the marking member and wherein the at least a portion of the second end extends into the opening when the marking member is in its depressed state; and
   a marking pad positioned on the second end of the marking member.

2. The device of claim 1, wherein the platform further comprises a channel extending from the opening to the first end of the marking member.

3. The device of claim 2, wherein at least a portion of a middle portion of the marking member extends into the channel when the marking member is in its depressed state.

4. The device of claim 1, wherein the handle further comprises a radiopaque marking.

5. The device of claim 1, wherein the platform further comprises a radiopaque marking.

6. The device of claim 5, wherein the radiopaque marking comprises a radiopaque ring positioned around the opening.

7. The device of claim 1, wherein the marking member further comprises a radiopaque marking positioned on the marking member.

8. The device of claim 1, wherein the marking member has a top side and a bottom side and wherein marking pad is positioned on the bottom side of the marking member.

9. A skin marking device comprising:
   a handle;
   a platform positioned in communication with the handle;
   a marking member, having a first end and a second end, extending from the handle, wherein the marking member has a raised state and a depressed state, the first end of the marking member is connected to the handle, and the second end of the marking member is substantially parallel to and spaced apart from the platform when the marking member is in its raised state;
   an opening positioned in the platform, wherein the opening is sized to receive at least a portion of the second end of the marking member and wherein the at least a portion of the second end extends into the opening when the marking member is in its depressed state; and
   a marking pad positioned on the second end of the marking member.

10. The device of claim 9, wherein the platform further comprises a channel extending from the opening to the first end of the marking member.

11. The device of claim 10, wherein at least a portion of a middle portion of the marking member extends into the channel when the marking member is in its depressed state.

12. The device of claim 9, wherein the handle further comprises a radiopaque marking.

13. The device of claim 9, wherein the platform further comprises a radiopaque marking.

14. The device of claim 13, wherein the radiopaque marking comprises a radiopaque ring positioned around the opening.

15. The device of claim 9, wherein the marking member further comprises a radiopaque marking positioned on the marking member.

16. The device of claim 9, wherein the marking member has a top side and a bottom side and wherein marking pad is positioned on the bottom side of the second end of the marking member.

17. A skin marking device comprising:
   a platform;
   a marking member, having a first end and a second end, extending from the platform, wherein the marking member has a raised state and a depressed state, the first end of the marking members is connected to the platform, and the second end of the marking member is substantially parallel to and spaced apart from the platform when the marking member is in its raised state;
   an opening positioned in the platform, wherein the opening is sized to receive at least a portion of the second end of the marking member and wherein the at least a portion of the second end extends into the opening when the marking member is in its depressed state; and
   a marking pad positioned on the second end of the marking member.

18. The device of claim 17, wherein the platform further comprises a channel extending from the opening to the first end of the marking member.

19. The device of claim 18, wherein at least a portion of the marking member extends into the channel when the marking member is in its depressed state.

20. The device of claim 17, wherein the platform further comprises a radiopaque marking.

21. The device of claim 20, wherein the radiopaque marking comprises a radiopaque ring positioned around the opening.

22. The device of claim 17, wherein the marking member further comprises a radiopaque marking.

23. The device of claim 17, wherein the marking member has a top side and a bottom side and wherein the marking pad is positioned on the bottom side of the second end of the marking member.

24. A skin marking device comprising:
a handle;
a disk-shaped platform positioned at an end of the handle;
a marking member, having a first end and a second end, extending from the handle, wherein the marking member has a raised state and a depressed state, the first end of the marking member is connected to the handle, the second end of the marking member is circular in shape, and the second end of the marking member is substantially parallel to and spaced apart from the disk-shaped platform when the marking member is in its raised state;
a circular opening centered in the disk-shaped platform, the circular opening having a diameter not smaller than the diameter of the second end of the marking member;
a channel positioned in the disk-shaped platform and extending from the circular opening to the first end of the marking member, wherein at least a portion of the marking member extends into the channel and the circular opening when the marking member is in its depressed state; and
a marking pad positioned on a bottom side of the second end of the marking member.

25. The device of claim 18, further comprising:
a radiopaque marking positioned on the handle.

26. The device of claim 18, further comprising:
a plurality of radiopaque markings positioned on the platform in the shape of a crosshair.

27. The device of claim 18, further comprising:
a radiopaque marking positioned on the marking member.

28. The device of claim 18, further comprising:
a radiopaque ring positioned around the circular opening.

* * * * *